United States Patent

Broger et al.

Patent Number: 5,508,438
Date of Patent: *Apr. 16, 1996

[54] PHOSPHORUS COMPOUNDS

[75] Inventors: Emil A. Broger, Magden; Marco Cereghetti, Basel, both of Switzerland

[73] Assignee: Hoffmann-La Roche Inc., Nutley, N.J.

[*] Notice: The term of this patent shall not extend beyond the expiration date of Pat. No. 5,274,125.

[21] Appl. No.: 122,426

[22] PCT Filed: Jan. 22, 1993

[86] PCT No.: PCT/CH93/00016

§ 371 Date: Sep. 24, 1993

§ 102(e) Date: Sep. 24, 1993

[87] PCT Pub. No.: WO93/15089

PCT Pub. Date: Aug. 5, 1993

[30] Foreign Application Priority Data

Jan. 31, 1992 [CH] Switzerland ................. 290/92
Jan. 18, 1993 [CH] Switzerland ................. 132/93

[51] Int. Cl.⁶ .................. C07D 333/02; C07F 9/28; C07F 9/02
[52] U.S. Cl. ............... 549/6; 548/412; 549/216; 568/12; 568/13; 568/17
[58] Field of Search ............... 549/6, 216; 568/12, 568/13, 17; 548/412

[56] References Cited

U.S. PATENT DOCUMENTS

| | | | |
|---|---|---|---|
| 4,556,740 | 12/1985 | Hansen et al. | 568/13 |
| 4,691,037 | 9/1987 | Yoshikawa et al. | 544/64 |
| 5,021,593 | 6/1991 | Nohira et al. | 556/20 |
| 5,087,728 | 2/1992 | Nohira et al. | 560/41 |
| 5,274,125 | 12/1993 | Broger et al. | 549/216 |

FOREIGN PATENT DOCUMENTS

| | | |
|---|---|---|
| 104375 | 4/1984 | European Pat. Off. |
| 408338 | 1/1991 | European Pat. Off. |
| 9216536 | 10/1992 | WIPO |

OTHER PUBLICATIONS

Noyori et al., Chemica Scripta, 25: pp. 83–89 (1985).

Yoshikawa, et al, Tetrahedron:Asymmetry, vol. 3, No. 1 pp. 13–16 (1992).

Primary Examiner—Cecilia Tsang
Attorney, Agent, or Firm—George M. Gould; William H. Epstein; Bruce A. Pokras

[57] ABSTRACT

Novel, racemic and optically active phosphorus compounds of the formula

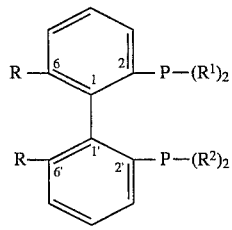

wherein R signifies lower alkyl, lower alkoxy, hydroxy or a protected hydroxy group, $R^1$ and $R^2$ are different from each other and represent lower alkyl, cycloalkyl, aryl, a five-membered heteroaromatic or a group of the formula

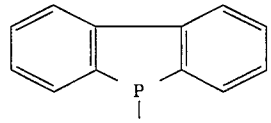

are described.

The compounds of formula I are useful in the form of complexes with a metal of Group VIII as catalysts for asymmetric hydrogenations and for enantioselective hydrogen displacements in prochiral allylic systems.

10 Claims, No Drawings

PHOSPHORUS COMPOUNDS

The present invention is concerned with novel, racemic and optically active phosphorus compounds of the general formula

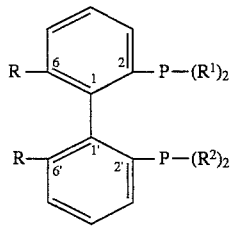
I wherein R signifies lower alkyl, lower alkoxy, hydroxy or a protected hydroxy group, $R^1$ and $R^2$ are different from each other and represent lower alkyl, cycloalkyl, aryl, a five-membered heteroaromatic or a group of the formula

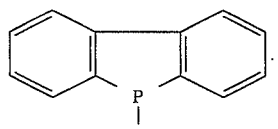

The invention is also concerned with the manufacture of the phosphorus compounds of formula I and with their use for enantioselective reactions such as e.g. asymmetric hydrogenations, enantioselective hydrogen displacements in prochiral, allylic systems, and the like.

The term "lower alkyl" signifies in the scope of the present invention straight-chain or branched alkyl groups with 1 to 4 carbon atoms such as methyl, ethyl, propyl, isopropyl, n-butyl, isobutyl and tert.butyl. The term "lower alkoxy" signifies groups in which the alkyl residue has the foregoing significance. As protecting groups for the hydroxy group there especially come into consideration in the scope of the present invention the usual ether-forming groups such as e.g. benzyl, allyl, benzyloxymethyl, lower alkoxymethyl or also 2-methoxyethoxymethyl and the like. The term "cycloalkyl" signifies three- to seven-membered rings such as cyclopropyl, cyclobutyl, cyclopentyl, cyclohexyl and cycloheptyl, especially cyclopentyl and cyclohexyl. The term "aryl" signifies in the scope of the present invention especially the phenyl residue which can be not only unsubstituted but also multiply-substituted in the ortho-, meta- or para-position. Substituents which come into consideration in this case are phenyl, lower alkyl or lower alkoxy groups, preferably methyl or methoxy groups, or also di-lower alkyl-amino, preferably dimethylamino, groups, as well as fluorine or also trialkylsilyl such as trimethylsilyl and the like. The term can, moreover, also signify naphthyl. The term "five-membered heteroaromatic" stands in the scope of the present invention for a substituent of the formula

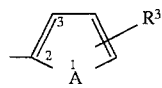
(a)

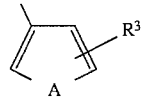
(b)

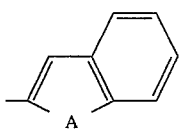
(c)

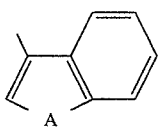
(d)

Furthermore, in the substituents of formulae (a) to (d) A signifies oxygen, sulphur or —$NR^4$. The substituent $R^3$ signifies hydrogen, lower alkyl, especially methyl, or lower alkoxy, especially methoxy, and $R^4$ stands for lower alkyl, preferably methyl.

Under the term "leaving group" used hereinafter there are to be understood in the scope of the present invention groups such as e.g. halogen, especially chlorine and bromine, as well as alkoxy groups such as methoxy and the like.

The phosphorus compounds of formula I can be present not only in racemic form but also in optically active form. Preferred compounds of formula I are those in which R signifies methoxy or methyl. Further, there are also preferred those in which $R^1$ and $R^2$ represent phenyl, p-tolyl, cyclopentyl, cyclohexyl, 2- or 3-furyl or 2-thienyl. Especially preferred compounds of formula I are:

(RS)-P,P-Dicyclohexyl-P',P'-diphenyl-(6,6'-dimethyl-biphenyl- 2,2'-diyl)diphosphine, (R)- or (S)-P,P-dicyclohexyl-P',P'-diphenyl-(6,6'-dimethyl-biphenyl- 2,2'-diyl)diphosphine, (RS)-P,P-dicyclohexyl-P',P'-di-p-tolyl-(6,6'-dimethyl-biphenyl- 2,2'-diyl)diphosphine, (R)- or (S)-P,P-dicyclohexyl-P',P'-di-p-tolyl-(6,6'-dimethyl-biphenyl- 2,2'-diyl)diphosphine, (RS)-P,P-diphenyl-P',P'-di-2-thienyl-(6,6'-dimethyl-biphenyl- 2,2'-diyl)diphosphine, (R)- or (S)-P,P-diphenyl-P',P'-di-2-thienyl-(6,6'-dimethyl-biphenyl- 2,2'-diyl)diphosphine, as well as the corresponding 6,6-dimethoxybiphenyls.

The compounds of formula I in accordance with the invention can be manufactured in a manner known per se. This can be carried out e.g. by reacting a racemic or optically active compound of the general formula

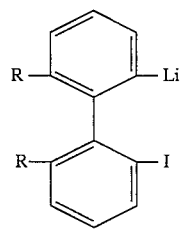
II wherein R has the above significance, with a compound of the general formula

Y—P($R^1$)$_2$    III wherein $R^1$ has the above significance and Y represents a leaving group, reacting a thus-obtained compound of the general formula

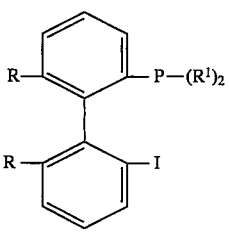

wherein R and $R^1$ have the above significance, with an alkyllithium to give a compound of the formula

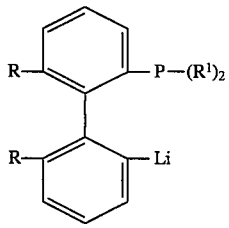

wherein R and $R^1$ have the above significance, reacting this with a compound of the general formula $$Y—P(R^2)_2 \qquad\qquad VI$$

wherein $R^2$ and Y have the above significance, and, for the manufacture of a compound of formula I in which R signifies hydroxy, subjecting a corresponding compound of formula I in which R represents lower alkoxy to an ether cleavage.

The reaction of a compound of formula II with a compound formula III can be carried out in a manner known per se. The reaction is conveniently carried out in an inert, aprotic organic solvent such as e.g. an aromatic hydrocarbon such as benzene, toluene etc., a liquid aliphatic hydrocarbon such as pentane, hexane etc. or in an ether such as, for example, diethyl ether, tetrahydrofuran, dimethoxyethane and the like or also a mixture of any of these solvents. The reaction is also conveniently carried out at a temperature of about room temperature to about –80° C. The pressure is not of critical significance and the reaction can be carried out readily at atmospheric pressure.

The reaction of a compound of formula IV with an alkyllithium to give a compound of formula V is preferably carried out using n-butyllithium, but especially using tert-.butyllithium. The reaction can be carried out in the previously mentioned solvents. The temperature is conveniently from about –50° C. to about –120° C., preferably from about –60° C. to about –80° C. The pressure is also not critical in this case and the reaction can therefore be carried out readily at atmospheric pressure.

The reaction of a compound of formula V with a compound of formula VI can be carried out analogously to the reaction of a compound of formula II with a compound III.

The ether cleavage of a compound of formula I in which R represents lower alkoxy can be carried out in a manner known per se, e.g. using boron tribromide and the like.

The compounds of formula II which are used as starting materials can be obtained readily in a manner known per se by treating the corresponding diiodo compounds with an alkyllithium such as, for example, n-butyllithium or, preferably, tert.butyllithium. The reaction conditions can be selected analogously to those used for the conversion of a compound of formula IV into a compound of formula V. In order to guarantee that only one iodine is replaced by lithium, the reaction is conveniently carried out using about equimolar amounts of reaction partners.

The previously mentioned diiodo compounds [not only in the (R,S) form but also in the (R) or (S) form] as well as the starting materials of formula III and VI are known compounds or analogues of known compounds which can be prepared readily in a manner known per se.

All of the previously mentioned reactions are conveniently carried out under an inert gas such as e.g. argon or nitrogen.

The phosphorus compounds of formula I in accordance with the invention form complexes with transition metals such as, for example, metals of Group VIII, especially with ruthenium, rhodium and iridium, which can be used as catalysts in asymmetric hydrogenations and also for enantioselective hydrogen displacements in prochiral, allylic systems. Ruthenium and rhodium complexes are preferred for the aforementioned hydrogenations, while rhodium complexes are preferred for isomerizations. These catalysts, i.e. the complexes from a metal of Group VIII and the phosphorus compounds of formula I, are novel and are also an object of the present invention.

The aforementioned complexes can be manufactured in a manner known per se, e.g. by reacting a compound of formula I with a compound, which can yield a metal of Group VIII, in a suitable, inert organic or aqueous solvent. As suitable compounds which yield e.g. rhodium there can be mentioned, for example, organic rhodium complexes with ethylene, propylene and the like, as well as with bis-olefins, e.g. (Z,Z)-1,5-cyclooctadiene, 1,5-hexadiene, bicyclco[2.2.1]hepta-2,5-diene or with other dienes which form readily soluble complexes with rhodium. Preferred compounds which yield rhodium are e.g. di-μ-chloro-bis[η⁴-(Z,Z)- 1,5-cyclooctadiene]dirhodium(I), di-μ-chloro-bis[η⁴-norbornadiene] dirhodium(I), di-μ-perfluoroacetato-bis[η⁴-(Z,Z)-1,5-cyclooctadiene] dirhodium(I), bis[η⁴-(Z,Z)-1,5-cyclooctadiene]-rhodium tetrafluoroborate or bis[η⁴-(Z,Z)-cyclooctadiene]rhodium perchlorate. Di-μ-chloro-bis[η⁴-(Z,Z)-1,5-cyclooctadiene]-diiridium(I) can be mentioned, for example, as a compound which yields iridium.

The aforementioned ruthenium complexes can be represented e.g. by the following formula $$Ru(Z)_2L \qquad\qquad VIII$$

wherein Z represents halogen or the group A—COO, A represents lower alkyl, aryl, halogenated lower alkyl or halogenated aryl and L represents a chiral diphosphine ligand of formula I.

These complexes can, in principle, be manufactured in a manner known per se. Conveniently and preferably, ruthenium complexes are manufactured, for example, by reacting a complex of the formula $$[Ru(Z^1)_2L^1{}_m]_p \cdot (H_2O)_q \qquad\qquad IX$$

wherein $Z^1$ represents halogen or a group $A^1$—COO, $A^1$ represents lower alkyl or halogenated lower alkyl, $L^1$ represents a neutral ligand, m represents the number 1, 2 or 3, p represents the number 1 or 2 and q represents the number 0 or 1, with a chiral diphosphine ligand of formula I or by reacting a ruthenium complex of the formula $$Ru(CF_3COO)_2L \qquad\qquad X$$

wherein L represents a chiral diphosphine ligand of formula I, with a salt which yields the anion Z in which Z has the above significance.

The term "neutral ligand" signifies in the scope of the present invention a readily exchangeable ligand such as, for example, a diolefin, e.g. norbornadiene, (Z,Z)-1,5-cyclooctadiene etc., or a nitrile such as acetonitrile, benzonitrile and the like. Where m represents the number 2 or 3, the ligands can be the same or different.

The ruthenium complexes of formula IX are known substances or analogues of known substances which can be obtained readily in a manner analogous to the preparation of the known substances, for example according to Albers, M. O. et al., J. Organomet. Chem. 272, C62-C66 (1984).

The reaction of a ruthenium complex of formula IX with a chiral diphosphine ligand of formula I can be carried out in a manner known per se. This reaction can be conveniently carried out in an inert organic solvent. As examples of such solvents there can be mentioned e.g. ethers such as tetrahydrofuran or dioxan, ketones such as, for example, acetone, lower alcohols such as, for example, methanol, ethanol etc., halogenated hydrocarbons such as methylene chloride, chloroform and the like, or also mixtures of such solvents. Moreover, the reaction can be carried out at a temperature between 0° C. and about 100° C., preferably between about 15° C. and about 60° C., but with the strict exclusion of oxygen.

The reaction of a ruthenium complex of formula X (obtainable from a complex of formula IX) with a salt which contains the anion Z can be carried out in a manner known per se. The term "a salt which yields the anion Z" signifies in the scope of the present invention, for example, ammonium salts, alkali metal salts or other suitable metal salts. In order to improve the solubility of such salts, crown ethers or the like can also be added in certain instances.

As mentioned earlier, the phosphorus compounds in accordance with the invention in the form of complexes with metals of Group VIII, especially rhodium and ruthenium, can be used, inter alia, for asymmetric hydrogenations. As especially suitable substrates there can be mentioned in this connection particularly allyl alcohols such as e.g. geraniol, 6,7-dihydrogeraniol, 6,7-dihydrofarnesol, 6,7,10,11-tetrahydrofarnesol and the like, as well as functionalized ketones such as β-ketoesters, e.g. methyl or ethyl acetoacetate etc., or also 2-pyridyl ketones such as e.g. 2-acetylpyridine, 2-pyridyl 2,8-bis(trifluoromethyl)-4-quinolyl ketone and the like.

In carrying out such hydrogenations, these complexes can firstly be manufactured and then added to a solution of the substance to be hydrogenated. Alternatively, however, they can also be manufactured in situ, e.g. in the presence of the substance to be hydrogenated.

The asymmetric hydrogenation can be carried out in a suitable organic solvent which is inert under the reaction conditions. As such solvents there can be mentioned especially aromatic hydrocarbons such as benzene, toluene etc., lower alcohols such as e.g. methanol or ethanol, water, esters such as ethyl acetate, halogenated hydrocarbons such as methylene chloride, chloroform and the like, cyclic ethers such as tetrahydrofuran or dioxan, and the like, or mixtures of such solvents.

The ratio of metal to ligand L conveniently lies between about 0.05 and about 5 mol and, respectively, between about 0.5 and about 2 mol, preferably at about 1 mol of metal per mol of ligand. The ratio of metal in the complexes such as e.g. of formula VIII to the substances to be hydrogenated conveniently lies between about 0.005 and about 1 mol. %, preferably between about 0.002 and about 0.1 mol. %.

The asymmetric hydrogenation with complexes such as e.g. of formula VIII is conveniently carried out at a temperature of about 0° C. to about 150° C. depending on the substrate which is used. This hydrogenation is also conveniently carried out under pressure, preferably at a pressure of about 2 to about 200 bar, particularly of about 10 to about 100 bar.

In analogy to the manufacture and use of the compounds of formula I, compounds of the binaphthyl type of the following formula

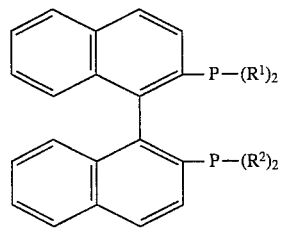

VII wherein $R^1$ and $R^2$ have the above significance, can also be manufactured and used. The binaphthyl rings can be substituted in the usual manner.

The following Examples illustrate the invention and do not in any manner represent a limitation. In these Examples the abbreviations have the following significances:
TLC thin-layer chromatography
GC capillary gas chromatography
e.e. enantiomeric excess. The e.e. of the hydrogenation products was determined by GC on a permethylated cyclodextrin phase.
RT room temperature
All temperatures are given in °Celsius.

EXAMPLE 1 a) 8.0 g (0.0162 mol) of (S)-diphenyl-(2'-iodo-6,6'-dimethyl-biphenyl- 2-yl)phosphine were dissolved in a mixture of 100 ml of absolute toluene, 200 ml of ether and 0.5 ml of triethylamine under Ar gasification, cooled to −65°, 12 ml of tert.butyllithium solution (1.6M in pentane; 0.019 mol) were added and the reaction mixture was stirred at −60° for 1 hour. Subsequently, 5.0 g (0.021 mol) of dicycylohexylchlorophosphine were added in one portion, rinsed in with a small amount of toluene and the grey-beige suspension was stirred at RT overnight. For the working-up, the mixture was treated with 50 ml of water and 50 ml of 3N NaOH, stirred for ¼ hour, extracted with 300 ml of toluene, the organic phase was washed once with 200 ml of water, dried ($Na_2SO_4$), filtered and evaporated. After recrystallization of the crude product from ethyl acetate there were obtained 6.2 g (68%) of (S)-P,P-dicyclohexyl-P',P'-diphenyl-( 6,6'-dimethylbiphenyl-2,2'-diyl)diphosphine as white crystals; m.p.: 185.4° (99.8% e.e. according to HPLC analysis on a Chiracel OD phase; GC content: 99.2%); $[\alpha]_D^{20}$+52.3 (c=1; $CHCl_3$).

In an analogous manner there was manufactured:
(R)-P,P-Dicyclohexyl-P',P'-diphenyl-(6,6'-dimethylbiphenyl- 2,2'-diyl)diphosphine; m.p.: 186°–186.9°; (99.8% e.e.; GC: 99.3%); $[\alpha]_D^{20}$−52.8 (c=1; $CHCl_3$).

b) The (R)- and (S)-diphenyl-(2'-iodo-6,6'-dimethylbiphenyl- 2-yl)phosphines used as the starting materials were prepared as follows:

32 ml of a tert.butyllithium solution (1.6M in pentane; 0.051 mol) were added to a solution, cooled to −76°, of 20.0 g (0.046 mol) of (R)-2,2'-diiodo-6,6'-dimethylbiphenyl (T. Frejd and T. Klingstedt, J. Chem. Soc., Chem. Commun. (1983) 1021) in 430 ml of absolute toluene and 90 ml of ether under Ar gasification and the mixture was stirred at −75° for ¾ hour. A solution of 20.1 g (0.092 mol) of chlorodiphenylphosphine in 100 ml of absolute toluene was subsequently added dropwise from a dropping funnel within ¼ hour, the mixture was stirred at –70° for 1 hour and, after removing the cooling bath, was stirred at RT overnight.

For the working-up, the reaction mixture, a grey-beige suspension, was treated with 150 ml of water, made alkaline with 80 ml of 3N NaOH and extracted with 300 ml of toluene. The organic phase was washed neutral twice with 200 ml of water each time, dried ($Na_2SO_4$) and evaporated, and the resulting residue (32.5 g; yellow oil) was chromatographed on 450 g of silica gel. In three main fractions there were eluted: with 4.5 l of hexane 3.2 g of unchanged starting material, with 15 l of hexane-toluene (95:5) mixture 13.1 g (71.3%) of enantiomer-pure monoiodide as white crystals and with 2 l of toluene 1.5 g of white crystalline (R)-(6,6'-dimethylbiphenyl-2,2'-diyl)bis(diphenylphosphine) (GC content: 75%). For analysis, the monoiodide (13.1 g) was recrystallized from ethyl acetate/methanol: (R)-diphenyl-(2'-iodo-6,6'-dimethylbiphenyl-2-yl)phosphine; m.p.: 167.5 –168.4°; $[\alpha]_D^{20}$–44.8 (c=1; $CHCl_3$).

In an analogous manner there was prepared:
(S)-Diphenyl-(2'-iodo-6,6'-dimethyl-1,1'-biphenyl-2-yl)phosphine; m.p.: 167.5°–168.7°; $[\alpha]_D^{20}$+43.5 (c=1; $CHCl_3$).

EXAMPLE 2

The following compounds were manufactured in an analogous manner to Example 1:
(R)-P,P-Dicyclohexyl-P',P'-di-p-tolyl-(6,6'-dimethylbiphenyl- 2,2'-diyl)diphosphine; m.p.: 167°; (98.6% e.e.; GC: 98%); $[\alpha]_D^{20}$–71.2 (c=1; $CHCl_3$);
(S)-P,P-dicyclohexyl-P',P'-di-p-tolyl-(6,6'-dimethylbiphenyl- 2,2'-diyl)diphosphine; m.p.: 166.1°; (97% e.e.; GC: 98%); [ $\alpha_D^{20}$+69.4 (c=1; $CHCl_3$);
(R)-P,P-diphenyl-P',P'-di-2-thienyl-(6,6'-dimethylbiphenyl-2,2'-diyl)diphosphine; m.p.: 151°–151.3°; (99.2% e.e.; GC: 99.5%); $[\alpha]_D^{20}$+71.9 (c=1; $CHCl_3$);
(S)-P,P-diphenyl-P',P'-di-2-thienyl-(6,6'-dimethylbiphenyl-2,2'-diyl)diphosphine; m.p.: 149°–150°; (99.9% e.e.; GC: 99.7%); $[\alpha]_D^{20}$– 70.2 (c=1; $CHCl_3$).

The following compounds used as the starting materials were prepared in an analogous manner to Example 2b):
(R)-Di-p-tolyl-(2'-iodo-6,6'-dimethylbiphenyl-2-yl)phosphine; m.p.: 135°–136°: $[\alpha]_D^{20}$–55.1 (c=1.0, $CHCl_3$);
(S)-di-p-tolyl-(2'-iodo-6,6'-dimethylbiphenyl-2-yl)phosphine; m.p.: 136.4°; $[\alpha]_D^{20}$+55.7 (c=1.0, $CHCl_3$);
(R)-dicyclohexyl-(2'-iodo-6,6'-dimethylbiphenyl-2-yl)phosphine; m.p.: 1.37°–139°, $[\alpha]_D^{20}$–8.6 (c=1, $CHCl_3$);
(S)-dicyclohexyl-(2'-iodo-6,6'-dimethylbiphenyl-2-yl)phosphine; m.p.: 138°–140°; $[\alpha]_D^{20}$+8.7 (c=$CHCl_3$).

EXAMPLE 3

The following compounds can be manufactured in an analogous manner to Examples 1 and, respectively, 2:
(S)-5-(2'-iodo-6,6'-dimethylbiphenyl-2-yl)-5H-benzo[b]-phosphindole; m.p. 173°–174°; $[\alpha]_D^{20}$+107.7 (c=1, $CHCl_3$);
(R)-5-(2'-iodo-6,6'-dimethylbiphenyl-2-yl)-5H-benzo[b]-phosphindole; m.p. 172°–174°; $[\alpha]_D^{20}$–106.8 (c=1, $CHCl_3$);
(S)-P,P-dicyclopentyl-P',P'-diphenyl-(6,6'-dimethylphenyl-2,2'-diyl)diphosphine; m.p. 129°–130°; $[\alpha]_D^{20}$+40.4 (c=5, $CHCl_3$);
(R)-P,P-dicyclopentyl-P',P'-diphenyl-(6,6'-dimethylphenyl-2,2'-diyl)diphosphine; m.p. 129°–130°; $[\alpha]_D^{20}$–39.5 (c=0, 6, $CHCl_3$);
(R)-5-(6,6'-dimethyl-2'-dicyclohexylphosphinobiphenyl-2-yl)- 5H-benzo[b]phosphindole; m.p. 164°–165°; $[\alpha]_D^{20}$–144.6 (c=0,7, $CHCl_3$);
(S)-5-(6,6'-dimethyl-2'-dicyclohexylphosphinobiphenyl-2-yl)- 5H-benzo[b]phosphindole; m.p. 163°–164°; $[\alpha]_D^{20}$+144 (c=0.7, $CHCl_3$);
(S)-P,P-diethyl-P',P'-diphenyl-(6,6'-dimethylbiphenyl-2,2'-diyl)diphosphine; m.p. 108°; $[\alpha]_D^{20}$+25.0 (c=1, $CHCl_3$);
(R)-P,P-diethyl-P',P'-diphenyl-(6,6'-dimethylbiphenyl-2,2'-diyl)diphosphine; m.p. 108°; $[\alpha]_D^{20}$–24.8 (c=1, $CHCl_3$);
(S)-P,P-di-2-furyl-P',P'-diphenyl-(6,6'-dimethylbiphenyl-2,2'-diyl)diphosphine; m.p. 125°; $[\alpha]_D^{20}$+66.7 (c=1, $CHCl_3$);
(R)-P,P-di-2-furyl-P',P'-diphenyl-(6,6'-dimethylbiphenyl-2,2'-diyl)diphosphine; m.p. 122.5°–123.3°; $[\alpha]_D^{20}$–66.3 (c=1, $CHCl_3$);
(R)-P,P-dicyclohexyl-P',P'-diphenyl-(6,6'-dimethoxybiphenyl- 2,2'-diyl)diphosphine;
(S)-P,P-dicyclohexyl-P',P'-diphenyl-(6,6'-dimethoxybiphenyl- 2,2'-diyl)diphosphine;
(S)-dicyclohexyl-(2'-iodo-6,6'-dimethoxybiphenyl-2-yl)phosphine;
(R)-dicyclohexyl-(2'-iodo-6,6'-dimethoxylbiphenyl-2-yl)phosphine;
(S)-5-(2'-iodo-6,6'-dimethoxybiphenyl-2-yl)-5H-benzo[b]-phosphindole;
(R)-5-(2'-iodo-6,6'-dimethoxybiphenyl-2-yl)-5H-benzo[b]-phosphindole;
(S)-P,P-dicyclopentyl-P',P'-diphenyl-(6,6'-dimethoxyphenyl- 2,2'-diyl)diphosphine;
(R)-P,P-dicyclopentyl-P',P'-diphenyl-(6,6'-dimethoxyphenyl- 2,2'-diyl)diphosphine;
(R)-5-(6,6'-dimethoxy-2'-dicyclohexylphosphinobiphenyl-2-yl)- 5H-benzo[b]phosphindole;
(S)-5-(6,6'-dimethoxy-2'-dicyclohexylphosphinobiphenyl-2-yl)- 5H-benzo[b]phosphindole;
(S)-P,P-diethyl-P',P'-diphenyl-(6,6'-dimethoxybiphenyl-2,2'-diyl)diphosphine;
(R)-P,P-diethyl-P',P'-diphenyl-(6,6'-dimethoxybiphenyl-2,2'-diyl)diphosphine;
(S)-P,P-di-2-furyl-P',P'-diphenyl-(6,6'-dimethoxybiphenyl-2,2'-diyl)diphosphine;
(R)-P,P-di-2-furyl-P',P'-diphenyl-(6,6'-dimethoxybiphenyl-2,2'-diyl)diphosphine;
(R)-P,P-dicyclohexyl-P',P'-di-p-tolyl-(6,6'-dimethoxybiphenyl-2,2'-diyl)diphosphine;
(S)-P,P-dicyclohexyl-P',P'-di-p-tolyl-(6,6'-dimethoxybiphenyl-2,2'-diyl)diphosphine;
(R)-P,P-diphenyl-P',P'-di-2-thienyl-(6,6'-dimethoxybiphenyl-2,2'-diyl)diphosphine;
(S)-P,P-diphenyl-P',P'-di-2-thienyl-(6,6'-dimethoxybiphenyl-2,2'-diyl)diphosphine.

EXAMPLE 4 a) 10.2 g (0.019 mol) of (R)-diphenyl-(2'-iodo-6,6'-dimethoxybiphenyl- 2-yl)phosphine were dissolved in a mixture of 150 ml of absolute toluene and 50 ml of ether under argon gasification, the solution was cooled to –70°, then treated with 15 ml of butyllithium solution (1.6M in hexane; 0.023 mol) and the reaction mixture was stirred at –69° for 45 minutes. Subsequently, 10.0 g (0.043 mol) of dicyclohexylchlorophosphine, dissolved in 50 ml of toluene, were added dropwise at –65° within 15 minutes and the grey-beige suspension was stirred at –65° for 1 hour and then at room temperature overnight. For the working-up, the mixture was treated with 85 ml of water and 15 ml of 3N NaOH, stirred for 15 minutes, extracted with 300 ml of toluene, the organic phase was washed twice with 150 ml of water, dried (Na$_2$SO$_4$), filtered and evaporated. After a chromatographic filtration on 400 g of silica gel (hexane/toluene 1:1) and recrystallization of the crude product from ethyl acetate, there were obtained 4.7 g of (R)-P,P-dicyclohexyl-P',P'-diphenyl-(6,6'-dimethoxybiphenyl- 2,2'-diyl)diphosphine [(R)-Cy$_2$MeOBIPHEP] as white crystals. M.p. 239.3°; [α]$_D^{20}$=+10.3 (c=1, CHCl$_3$).

In an analogous manner there was manufactured:
(S)-P,P-Dicyclohexyl-P',P'-diphenyl-(6,6'-dimethoxybiphenyl- 2,2'-diyl)diphosphine, [(S)-Cy$_2$MeOBIPHEP].

b) The (R)- and (S)-diphenyl-(2'-iodo-6,6'-dimethoxy-1,1'-biphenyl- 2-yl)phosphines used as the starting materials were prepared as follows:

18 ml of a tert.-butyllithium solution (15% solution in pentane; 0.028 mol) were added under argon gasification to a solution, cooled to −76°, of 13.7 g (0.029 mol) of (S)-2,2'-diiodo- 6,6'-dimethoxy-1,1'-biphenyl dissolved in 200 ml of absolute toluene and 50 ml of ether and the mixture was stirred at −70° for 1 hour. Subsequently, a solution of 13 g (0.062 mol) of chlorodiphenylphosphine in 50 ml of absolute toluene was added dropwise within 15 minutes from a dropping funnel, the mixture was stirred at −70° for 1 hour and, after removing the cooling bath, stirred at room temperature for 1 hour. For the working-up, the reaction mixture was treated with 70 ml of water, made alkaline with 30 ml of 3N NaOH and extracted with 500 ml of ethyl acetate. The organic phase was washed neutral with 150 ml of water, dried (Na$_2$SO$_4$), evaporated and the residue obtained was chromatographed on 300 g of silica gel. In two main fractions there were eluted: with 2.1 l of hexane/toluene (6:4) mixture 4.0 g of unchanged starting material and with 3.5 l of hexane/toluene (1:1) mixture 9.9 g of enantiomer-pure mono-iodide as white crystals which were used directly in the following step. About a further 120 mg of crystalline (S)-MeOBIPHEP could be isolated from the polar fractions. For analysis, a sample of the monoiodide was recrystallized from ethyl acetate/methanol:
(S)-Diphenyl-(2'-iodo-6,6'-dimethoxy-1,1'-biphenyl-2-yl)phosphine; m.p.: 125.7°; [α]$_D^{20}$=−9.0 (c=0.7; CHCl$_3$).

In an analogous manner there were prepared:
(R)-Diphenyl-(2'-iodo-6,6'-dimethoxy-1,1'-biphenyl-2-yl)phosphine;
(R,S)-diphenyl-(2'-iodo-6,6'-dimethoxy-1,1'-biphenyl-2-yl)phosphine; m.p.: 194.0°–194.4°.

c) The (R)- and (S)-2,2'-diiodo-6,6'-dimethoxy-1,1'-biphenyls used as the starting materials in b) were prepared as follows:

12.15 g (0.05 mol) of (S)-2,2'-diamino-6,6'-dimethoxy-1,1'-biphenyl were dissolved in a mixture of 288 ml of water and 100 ml of conc. sulphuric acid at about 30°–40° and the solution was cooled to 2° in a cooling bath. To this mixture was added at 2° within 30 minutes a solution of 9.6 g (0.140 mol) of sodium nitrite in 25 ml of water and, after completion of the addition, the mixture was stirred at 4° for 30 minutes. Subsequently, the mixture was treated with 150 ml of toluene, a solution of 42 g (0.253 mol) of potassium iodide and 16.8 g (0.1 mol) of iodine in 75 ml of water was added dropwise within 5 minutes from a dropping funnel and the mixture was stirred at room temperature for 3 hours. For the working-up, the reaction mixture was extracted with 300 ml of ethyl acetate and 200 ml of toluene, the organic phases were washed 2× with 200 ml of a 10% aqueous sodium thiosulphate solution each time and 2× with 150 ml of water each time, combined, dried (Na$_2$SO$_4$), evaporated and the resulting crude product was chromatographed on 150 g of silica gel. The product was eluted with 10 l of hexane/dichloromethane (4:1 to 1:1) mixture and recrystallized once from hexane to give 14.2 g of white crystalline enantiomer-pure (S)-2,2'-diiodo-6,6'-dimethoxy- 1,1'-biphenyl. M.p. 163.5°; [α]$_D^{20}$=55.1° (c=1; CHCl$_3$).

In an analogous manner there was prepared:
(R)-2,2'-diiodo-6,6'-dimethoxy-1,1'-biphenyl. M.p. 152°; [α]$_D^{20}$=54.4° (c=1; CHCl$_3$).

d) The (R)- and (S)-2,2'-diamino-6,6'-dimethoxy-1,1'-biphenyls used as the starting materials in c) were prepared as follows:

80 g (0.33 mol) of (rac)-2,2'-diamino-6,6'-dimethoxy-1,1'-biphenyl were dissolved in 600 ml of ethyl acetate and 150 g of (SS)-di(phenylaminocarbonyloxy)-succinic acid [(SS)-DIPACOSA] were dissolved in a mixture of 400 ml of ethyl acetate and 50 ml of methanol at about 60°, the two solutions were combined at 60° and left to stand at room temperature overnight for crystallization. After suction filtration, washing (150 ml of ethyl acetate) and drying (14 mm Hg; room temperature; 30 minutes) of the white crystallizate there were obtained 173.9 g of (S)-2,2'-diamino- 6,6'-dimethoxy-1,1'-biphenyl-(SS)-DIPACOSA (1:2)-associate. [(S)/(R) content: 99%/1%.

In order to improve the enantiomer separation, the crystallizate (173.9 g) was suspended in 300 ml of ethyl acetate, stirred at 60° for 15 minutes, the suspension was left to stand at room temperature overnight, suction filtered, the residue was washed with ethyl acetate (100 ml), dried (14 mm Hg/room temperature) and in this manner there were obtained 154 g of (1:2)-associate [(S)/(R) content: 99.7%/0.3%]. In order to separate the resolving agent, this material (154 g) was dissolved in 2 l of ethyl acetate, 700 ml of water were added thereto and the aqueous phase was adjusted to pH 8 with a sat. sodium bicarbonate solution while stirring. After separating the organic phase, which was washed (200 ml of water), dried (Na$_2$SO$_4$) and evaporated, there were obtained 30.9 g of oily (S)-2,2'-diamino-6,6'-dimethoxy-1,1'-biphenyl [(S)/(R) content: 99.8%/0.2%. [α]$_D^{20}$= −32.0° (c=1; CHCl$_3$).

In an analogous manner, starting from racemic diamine with (RR)-DIPACOSA there was obtained oily, (R)-2,2'-diamino-6,6'-dimethoxy- 1,1'-biphenyl which could be recrystallized from diethyl ether [(S)/(R)-content 0%/100%]. M.p. 86.9°; [α]$_D^{20}$=+32.8° (c=1; CHCl$_3$).

The following diphosphines were also manufactured in an analogous manner to the foregoing:
(S)-P,P-Dicyclopentyl-P',P'-diphenyl-(6,6'-dimethoxybiphenyl- 2,2'-diyl)diphosphine; [(S)-Cyp$_2$MeOBIPHEP]; m.p. 210.9°; [α]$_D^{20}$=−15.7° (c=0,4; CHCl$_3$).
(R)-P,P-dicyclopentyl-P',P'-diphenyl-(6,6'-dimethoxybiphenyl- 2,2'-diyl)diphosphine; [(R)-Cyp$_2$MeOBIPHEP];
(S)-P,P-diisopropyl-P',P'-diphenyl-(6,6'-dimethoxybiphenyl- 2,2'-diyl)diphosphine; [(S)-Ipr$_2$MeOBIPHEP]; m.p. 147.9°; [α]$_D^{20}$= −29° (c=0.5; CHCl$_3$).
(R)-P,P-diisopropyl-P',P'-diphenyl-(6,6'-dimethoxybiphenyl- 2,2'-diyl)diphosphine; [(R)-Ipr$_2$MeOBIPHEP];
(S)-P,P-diethyl-P',P'-diphenyl-(6,6'-dimethoxybiphenyl-2,2'-diyl)diphosphine; [α]$_D^{20}$=−40° (c=1, CHCl$_3$);
(R)-P,P-diethyl-P',P'-diphenyl-(6,6'-dimethoxybiphenyl-2,2'-diyl)diphosphine;
(S)-P,P-di-α-furyl-P',P'-diphenyl-(6,6'-dimethoxybiphenyl-2,2'-diyl)diphosphine; m.p. 213.9°; [α]$_D^{20}$=−28.4° (e=0.5, CHCl$_3$);
(R)-P,P-di-α-furyl-P',P'-diphenyl-(6,6'-dimethoxybiphenyl-2,2'-diyl)diphosphine;
(S)-P,P-di-α-thienyl-P',P'-diphenyl-(6,6'-dimethoxybiphenyl- 2,2'-diyl)diphosphine; m.p. 223.1°; [α]$_D^{20}$=−102° (c=0.5, CHCl$_3$);

(R)-P,P-di-α-thienyl-P',P'-diphenyl-(6,6'-dimethoxybiphenyl- 2,2'-diyl)diphosphine.

EXAMPLE 5 a) 10.2 mg (0.025 mmol) of bis-(1,5-cyclooctadiene)rhodium-(I) tetrafluoroborate, 14.1 mg (0.025 mmol) (R)-P,P-dicyclohexyl-P',P'-diphenyl-( 6,6'-dimethylbiphenyl-2,2'-diyl)diphosphine (manufactured according to Example 1) and 8.1 mg (0.025 mmol) of tetrabutylammonium bromide were suspended in 20 ml of toluene in a 50 ml glass flask in a glove box ($O_2$ content<1 ppm). The suspension was subsequently stirred for 60 minutes, whereby an orange, clear solution formed.

b) A 500 ml autoclave was loaded in a glove box ($O_2$ content< 1 ppm) with 14.8 g (40 mmol) of 2-pyridyl 2,8-bis(trifluoromethyl)- 4-quinolyl ketone, with the catalyst solution prepared above and with 134 ml of toluene. The hydrogenation was carried out at 60°, at a constant pressure of 60 bar $H_2$ and while stirring intensively. After a hydrogenation time of 19 hours the conversion was 100° (TLC). The hydrogenation solution was evaporated on a rotary evaporator at 45°/20 mbar. For the crystallization of the product, the residue (13.8 g) was dissolved in 21 ml of hot toluene, cooled slowly to RT and stirred for 16 hours. The crystallization was completed by cooling to 1° and stirring for 3 hours. The yellow crystals were filtered off, washed with cold toluene and dried for 18 hours and 50°/20 mbar. There were obtained 12.7 g (92%) of (R)-α-(2-pyridyl)-2, 8-bis(trifluoromethyl)- 4-quinolinemethanol; m.p. 130°–131°; 91.8% e.e.; $[\alpha]_D^{20}$+17.1 ° (c=1, MeOH).

Two-fold recrystallization from ethanol/water yielded pure (R) enantiomer [(S) isomer not detectable in the GC]; $[\alpha]_D^{20}$=+18.7° (c=1, MeOH); m.p.: 136.5°–137.7°.

We claim:

1. Racemic and optically active phosphorus compounds of the general formula:

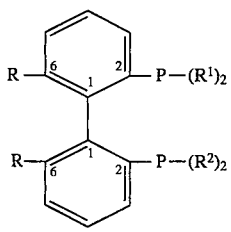

wherein R is lower alkyl, lower alkoxy, hydroxy or a protected hydroxy group;

$R^1$ and $R^2$ are different from each other and are lower alkyl, cycloalkyl, aryl, or a five-membered heteroaromatic group selected from the group consisting of:

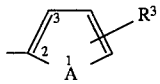 (a)

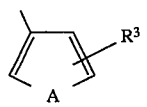 (b)

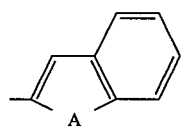 (c)

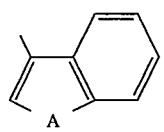 (d)

wherein A is oxygen, sulphur or —$NR^4$ wherein $R^4$ is lower alkyl, and $R^3$ is hydrogen, lower alkyl, or lower alkoxy;

or a group of the formula

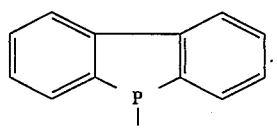

2. Racemic and optically active phosphorus compounds of formula I according to claim 1, wherein R signifies methoxy or methyl and $R^1$ and $R^2$ represent phenyl, p-tolyl, cyclopentyl, cyclohexyl, 2- or 3-furyl or 2-thienyl.

3. The compound of claim 1, wherein said compound is (R)- or (S)-P,P-Dicyclohexyl-P',P'-diphenyl-(6,6'-dimethylbiphenyl- 2,2'-diyl)diphosphine.

4. The compound of claim 1, wherein said compound is (R)- or (S)-P,P-Dicyclohexyl-P',P'-di-p-tolyl-(6,6'-dimethylbiphenyl- 2,2'-diyl)diphosphine.

5. The compound of claim 1, wherein said compound is (R)- or (S)-P,P-Diphenyl-P',P'-di-2-thienyl-(6,6'-dimethylbiphenyl- 2,2'-diyl)diphosphine.

6. The compound of claim 1, wherein said compound is (R)- or (S)-P,P-Dicyclohexyl-P',P'-diphenyl-(6,6'-dimethoxybiphenyl- 2,2'-diyl)diphosphine.

7. The compound of claim 1, wherein said compound is (R)- or (S)-P,P-Dicyclopentyl-P',P'-diphenyl-(6,6'-dimethoxybiphenyl- 2,2'-diyl)diphosphine.

8. The compound of claim 1, wherein said compound is (R)- or (S)-P,P-Diisopropyl-P',P'-diphenyl-(6,6'-dimethoxybiphenyl- 2,2'-diyl)diphosphine.

9. The compound of claim 1, wherein said compound is (R)- or (S)-P,P-Di-α-furyl-P',P'-diphenyl-(6,6'-dimethoxybiphenyl- 2,2'-diyl)diphosphine.

10. The compound of claim 1, wherein said compound is (R)- or (S)-P,P-Di-α-thienyl-P',P'-diphenyl-(6,6'-dimethoxybiphenyl- 2,2'-diyl)diphosphine.

* * * * *